(12) United States Patent
Itai et al.

(10) Patent No.: US 6,308,145 B1
(45) Date of Patent: *Oct. 23, 2001

(54) METHODS FOR SEARCHING STABLE DOCKING MODELS OF BIOPOLYMER-LIGAND MOLECULE COMPLEX

(75) Inventors: Akiko Itai, 16-6, Hongo 5-chome, Bunkyo-ku, Tokyo 113; Miho Mizutani, Tokyo, both of (JP)

(73) Assignee: Akiko Itai, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/761,345

(22) Filed: Dec. 6, 1996

Related U.S. Application Data

(62) Division of application No. 08/307,581, filed on Sep. 27, 1994.

(30) Foreign Application Priority Data

Mar. 27, 1998 (JP) .................................................. 4-119484

(51) Int. Cl.[7] .................................................. G06T 17/40

(52) U.S. Cl. ............................................................. 703/12

(58) Field of Search .................................... 364/496, 499, 364/497, 578, DIG. 1, 223.4, DIG. 2, 924.3; 395/161; 702/27; 435/6; 514/473; 345/398; 703/12

(56) References Cited

U.S. PATENT DOCUMENTS 4,908,773  * 3/1990  Pantoliano et al. .................. 364/496
5,331,573  * 7/1994  Balaji et al. ..................... 364/497 X (List continued on next page.)

OTHER PUBLICATIONS

Imberty et al. "Molecular Modelling of Protein–Carbohydrate Interactions. Docking of Monosaccharides in the Binding Site of Concenavalin A" Glycobiology v. 1 N. 6 pp. 631–642, 1991.*

(List continued on next page.)

*Primary Examiner*—M. Kemper
(74) *Attorney, Agent, or Firm*—Oblon, Spivak, McClelland, Maier & Neustadt, P.C.

(57) ABSTRACT

Methods for searching stable docking models of biopolymer-ligand molecule complex, which comprise the steps of: (1) searching possible hydrogen-bond schemes between a biopolymer and a ligand molecule by preparing possible combination sets of hydrogen-bonding heteroatoms in the ligand molecule with dummy atoms located at the positions of heteroatoms that can be hydrogen-bond partners to hydrogen-bonding functional groups in the biopolymer; (2) estimating the possible the hydrogen-bond schemes between the biopolymer and ligand molecule and the possible conformations of a hydrogen-bonding part of the ligand molecule at the same time by comparing the distances between the dummy atoms with the distances between the hydrogen-bonding heteroatoms; and (3) obtaining the possible docking models of the biopolymer-ligand molecule complex by changing the coordinates of all atoms of the ligand molecule into the coordinate system of the biopolymer, according to the correspondences between the hydrogen-bonding heteroatoms in the ligand molecule and the dummy atoms in combination sets for each of the hydrogen-bond schemes and conformations obtained in the second step are provided. According to the methods of the present invention, the structures of stable biopolymer-ligand molecule complex can be searched efficiently and precisely in a short time.

8 Claims, 9 Drawing Sheets

U.S. PATENT DOCUMENTS

| | | | | |
|---|---|---|---|---|
| 5,386,507 | * | 1/1995 | Teig et al. ............................. | 345/348 |
| 5,495,423 | * | 2/1996 | Delisi et al. ......................... | 364/496 |
| 5,496,938 | * | 3/1996 | Gold et al. ........................... | 435/6 X |
| 5,585,397 | * | 12/1996 | Tung et al. .......................... | 514/473 |
| 5,642,292 | * | 6/1997 | Itai et al. .............................. | 702/27 |

OTHER PUBLICATIONS

Van Vlijmen et al. "Molecular Modeling of Putative Antagonist Binding Site on Helix III of the Beta–Adrenoceptor" J. Comput. Aided Mol. Des. 3(2) pp. 165–74, Jun. 1989.*

Naruto et al. "Computer Assisted Analysis of Bioactivity" Eur. J. Med. Chem. 20 n. 6 pp. 533–40, 1985.*

Yue, "Distance–Constrained Molecular Docking by Simulated Annealing" Protein Engineering pp. 177–184 v. 4 n. 2, 1990.*

Jiang et al. "'Soft Docking': Matching of Molecular Surface Cubes" J. Mol. Biol. pp. 79–102, 1991.*

Cache User's Guide, Version 2, Tektronix Inc., 1989.*

* cited by examiner

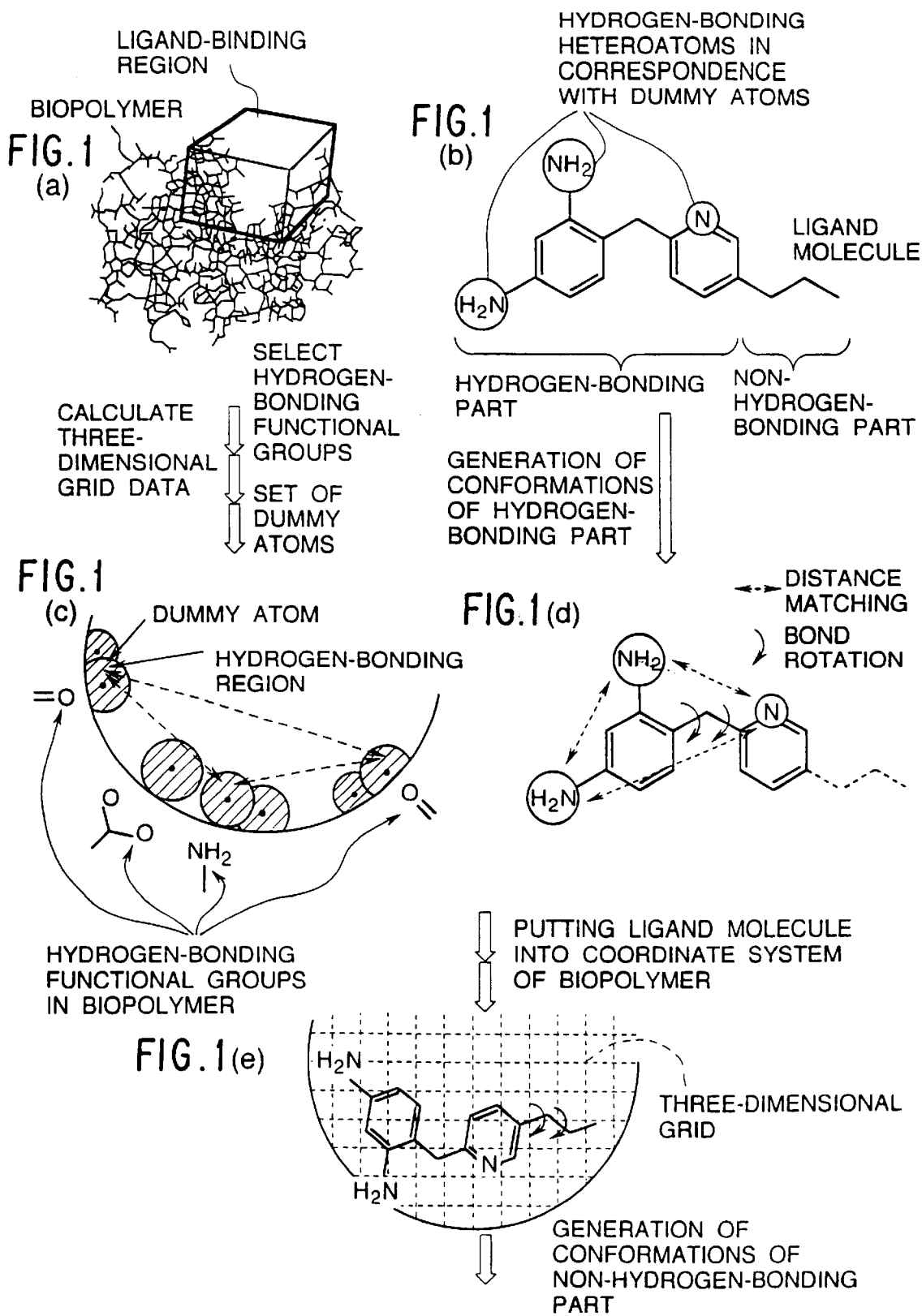

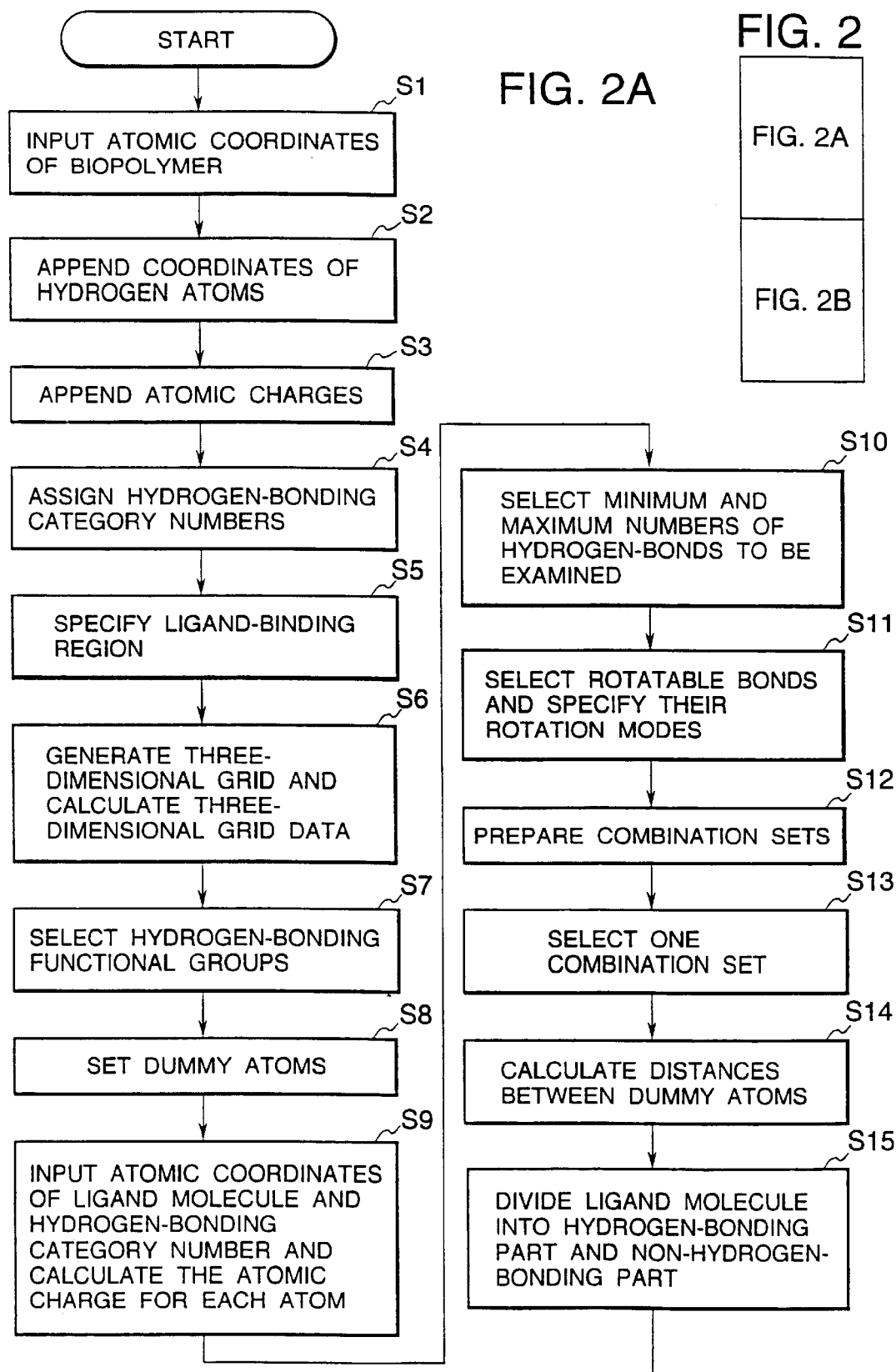

METHOTREXATE

DIHYDROFOLATE

FIG. 5(a) INPUT CONFORMATION (UNBOUND CRYSTAL STRUCTURE) −139.1°

FIG. 5(b) CONFORMATION IN THE LOWEST ENERGY DOCKING MODEL OF DHFR-MTX COMPLEX 25.3°

FIG. 5(c) CONFORMATION IN THE CRYSTAL STRUCTURE OF DHFR-MTX COMPLEX 28.4°

CONFORMATION OF METHOTREXATE

STEREOSPECIFICITY OF DHFR ENZYMATIC REACTION

DIHYDROFOLATE (DHF)

TETRAHYDROFOLATE (DHFR ENZYMATIC REACTION PRODUCT)

THE LOWEST ENERGY DOCKING MODEL OF DHFR-DHF COMPLEX

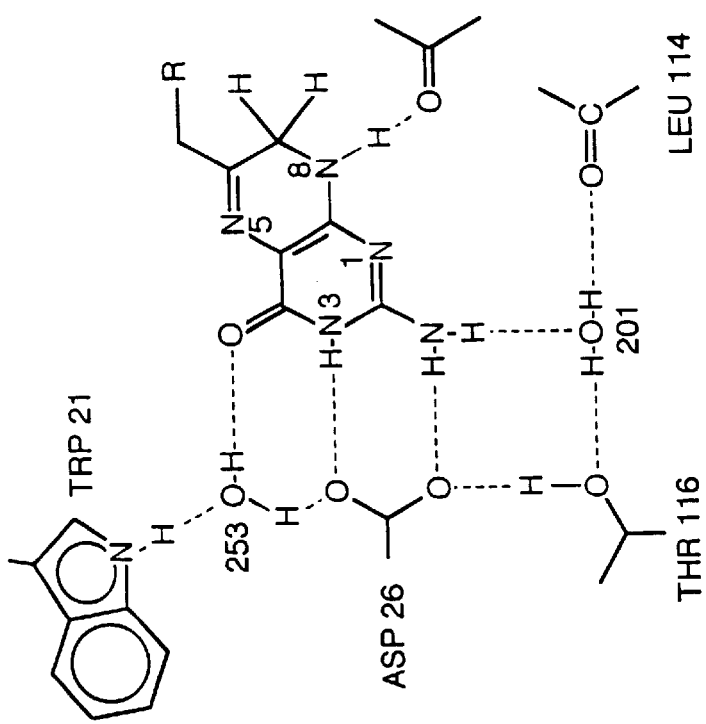
FIG. 8(a) BINDING MODE OF MTX IN THE CRYSTAL STRUCTURE OF DHFR-MTX COMPLEX
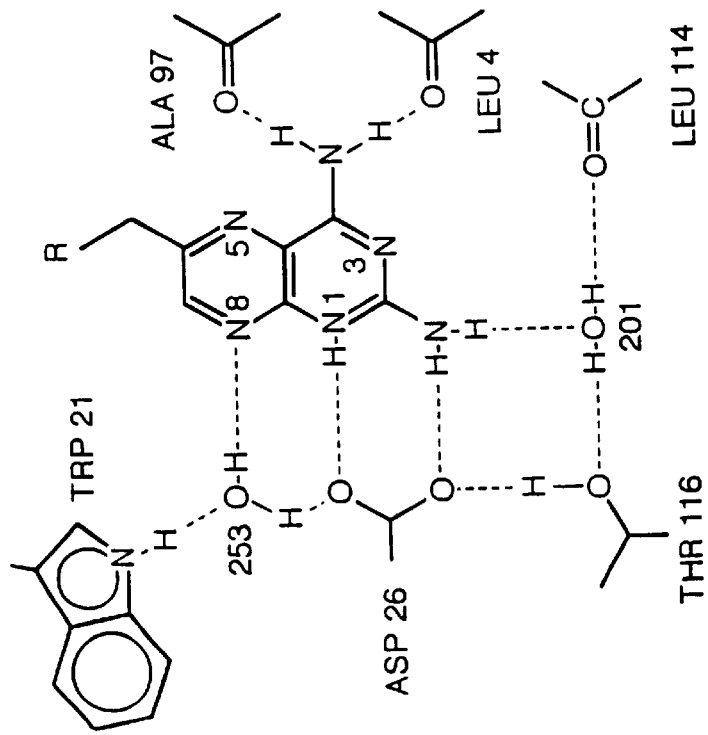
FIG. 8(b) BINDING MODE OF DHF PREDICTED FROM THE STEREOSPECIFICITY OF DHFR ENZYMATIC REACTION PRODUCT

METHODS FOR SEARCHING STABLE DOCKING MODELS OF BIOPOLYMER-LIGAND MOLECULE COMPLEX

This is a Division of application Ser. No. 08/307,581 filed on Sep. 27. 1994, now pending, which was filed as International Application No. PCT/JP93/00365 filed on Mar. 26, 1993.

TECHNICAL FIELD

The present invention relates to methods for searching stable docking models of biopolymer-ligand molecule complex that can be utilized in designing the structures of drugs, pesticides, and other biologically active compounds.

BACKGROUND ART

Strong binding of drugs and biologically active substances to their target biopolymers is required for the appearances of their bioactivities. The biopolymers include pharmacological receptors which take part in signal transmission between cells, as well as enzymes, cytokines and other proteins, complexes comprising these proteins as main components, and nucleic acids. Since 1960, the steric structures of a large number of biopolymers have been revealed at the atomic level by X-ray crystallographic analyses and the structural data thereof have been stored in the Protein Data Bank and published.

Small molecules which can be bound to these biopolymers are called ligand molecules. The ligand molecules include candidate molecules for drugs such as drug molecules to be synthesized in future, as well as drugs, substrates and inhibitors of enzymes, coenzymes and the like.

For the stable binding between the biopolymers and ligand molecules it is required that the shapes of cavities which exist in the steric structures of biopolymers and into which ligand molecules are bound (hereinafter referred to as "ligand-binding sites") should be complementary to the shapes of the ligand molecule surfaces as in the case of locks and keys and that there should be interactions between the both molecules which result in specific affinity therebetween. It is known from the crystallographic analyses of biopolymer-ligand molecule complexes that among these intermolecular interactions, hydrogen-bond, electrostatic and hydrophobic interactions and the like are particularly important. In drug design and structure-activity relationship study, it is very important to know whether a compound molecule can form a stable complex with its target biopolymer and, if so, what kind of binding mode the complex has (i.e., which functional group in the ligand-binding site of the biopolymer interact which functional groups in the ligand molecule in what kind of mode) and how stable the complex is. In conformationally flexible ligand molecules, it is also important for drug design to determine the conformation of the ligand molecules bound to target biopolymers (active conformation) and such a determination must be made at the same time as searching stable binding modes.

It is known that when the complexes have the most stable structures in terms of free energy, the ligand molecule structures are often different from the crystal structures of unbound ligand molecules, the structures in solutions, and the energically most stable (or any local minimum) structures obtained by various kinds of energy calculations.

It is impossible to determine the modes of binding of all ligand molecules of interest to their target biopolymer by experimental methods such as X-ray crystallographic analysis. First, this is because a great effort and time are necessary for analyzing the mode of binding of each ligand molecule to the biopolymer by experimental methods. In addition, if the ligand molecules are substrates for enzymes, any stable structures of the complex can not be detected in the experiments due to the progress of enzymatic reactions. Furthermore, the samples of the ligand compounds are often unavailable if they exist. In some cases, it may be required to predict the binding mode and the stability of the complex between an imaginary ligand molecule and its biopolymer, in order to decide whether it is valuable to synthesize the ligand molecule. Such a prediction is very useful in making new drugs and biologically active substances by molecular design.

The simulation study of the mode of stable binding of ligand molecules to their target biopolymer whose structure is known is called "docking study". In the past, the docking study was performed using molecular models, but the use of molecular models had problems in that; it needed much time and effort to construct the molecular models, that the precision of the molecular models and the reproducibility of results were poor and that quantitative results could not be obtained. As a method for solving these problems, a simulation method using a computer and computer graphics is generally used today.

In the simulation method using a computer and computer graphics, it is the most common procedure that initial structures of complexes are roughly set interactively on computer graphics displays by visual decision and then they are refined and quantitated by computation methods. However, there are an enormous number of possible docking structures, and therefore it is very difficult to reach objectively the correct solution. Furthermore, it is a time-consuming and laborious method. In addition, the obtained results are unreliable and unreproducible in that they vary with users.

In order to solve these problems, a few methods in which user's preconception can be eliminated have been studied. Kuntz et al. published a program for approximately representing ligand molecules by sets of spheres and changing the relative positions between the spheres instead of changing the molecular conformations to determine whether the ligand molecules fit the ligand-binding site in a receptor (Docking Flexible Ligands to Macromolecular Receptors by Molecular Shape, R. L. Desjarlais, R. P. Sheridan, J. Scott Dixon, I. D. Kuntz and R. Venkataraghavan: J. Med Chem. (1986) 29, pp.2149–2153). However, this program is not effective in determining the binding modes and the ligand conformations in stable complexes in a reliable manner because it does not deal with specific intermolecular interactions such as hydrogen-bond and the like.

F. Jiang et al. developed an automatic docking method in which intermolecular interactions such as hydrogen-bond, electrostatic interaction and the like are considered qualitatively in addition to the shape complementarity which Kuntz et al. highlighted (F. Jiang and S. Kim, J. Mol. Biol. 219, 79 (1991)). However, this method neither considers the conformational flexibility of ligand molecules nor makes a sufficient quantitative estimate of intermolecular interactions.

None of other methods are effective because they have problems in that they do not consider specific intermolecular interactions or the conformational flexibility of ligand molecules. The binding mode of ligand molecules to biopolymers and the ligand conformations are coupled completely. Since the binding mode and active conformation have enormous numbers of possibilities, all the combinations thereof must be examined in order to obtain the most stable structure of the complex covering all possible binding modes and ligand conformations. However, no methods for searching stable structures of complexes that take into account all the combinations of the binding modes and ligand conformations have been established.

Therefore, an object of the present invention is to provide methods for searching stable docking models of biopolymer-ligand molecule complex that solve the above-mentioned problems.

Another object of the present invention is to provide methods for searching the modes of binding of ligand molecules to biopolymers and the active conformations of the ligand molecules at the same time.

DISCLOSURE OF INVENTION

As a result of various studies, the inventors developed methods for docking automatically any ligand molecules to the ligand-binding sites in biopolymers by searching the binding modes of stable complexes and the active conformations of the ligand molecules at the same time by taking into account hydrogen-bond, electrostatic interaction and van der Waals force as the interactions between the biopolymers and the ligand molecules, and they succeeded in solving the above-mentioned problems.

The present invention provides methods for searching stable docking models of biopolymer-ligand molecule complex, which comprise the steps of: (1) searching possible hydrogen-bond schemes between a biopolymer and a ligand molecule by preparing possible combination sets of hydrogen-bonding heteroatoms in the ligand molecule with dummy atoms located at the positions of heteroatoms that can be hydrogen-bond partners to hydrogen-bonding functional groups in the biopolymer; (2) estimating the possible hydrogen-bond schemes between the biopolymer and ligand molecule and the possible conformations of a hydrogen-bonding part of the ligand molecule at the same time by comparing the distances between the dummy atoms with the distances between the hydrogen-bonding heteroatoms; and (3) obtaining the possible docking models of the biopolymer-ligand molecule complex by changing the coordinates of all atoms of the ligand molecule into the coordinate system of the biopolymer, according to the correspondences between the hydrogen-bonding heteroatoms in the ligand molecule and the dummy atoms in combination sets for each of the hydrogen-bond schemes and conformations obtained in the second step.

In addition, the present invention provides methods for searching stable docking models of biopolymer-ligand molecule complex, which comprise the steps of: (1) searching possible hydrogen-bond schemes between a biopolymer and a ligand molecule by preparing possible combination sets of hydrogen-bonding heteroatoms in a partial structure of the ligand molecule and dummy atoms located at the positions of heteroatoms that can be hydrogen-bond partners to hydrogen-bonding functional groups in the biopolymer; (2) estimating the possible hydrogen-bond schemes between the biopolymer and ligand molecule and the possible conformations of the partial structure in the ligand molecule at the same time by comparing the distances between the dummy atoms with the distances between the hydrogen-bonding heteroatoms; (3) specifying on the basis of the hydrogen-bond schemes and conformations obtained in the second step, those combination sets of the hydrogen-bonding heteroatoms and dummy atoms which provide hydrogen-bond schemes that are impossible in the partial structure of the ligand molecule, and hydrogen-bonding heteroatoms that cannot form any hydrogen-bond with the dummy atoms; (4) searching possible hydrogen-bond schemes between the biopolymer and the whole ligand molecule by preparing possible combination sets of the dummy atoms and the hydrogen-bonding heteroatoms in the whole ligand molecule excluding the combination sets containing the hydrogen-bonding heteroatoms specified in the third step and the combination sets of the dummy atoms and hydrogen-bonding heteroatoms that are specified in the third step; (5) estimating the hydrogen-bonding schemes between the biopolymer and ligand molecule and the conformations of a hydrogen-bonding part of the ligand molecule at the same time by comparing the distances between the dummy atoms with the distances between the hydrogen-bonding heteroatoms in the ligand molecules; and (6) obtaining possible docking models of the biopolymer-ligand molecule complex by changing the coordinates of all atoms of the ligand molecule into the coordinate system of the biopolymer, according to the correspondences between the hydrogen-bonding heteroatoms in the ligand molecule and the dummy atoms in combination sets for each of the hydrogen-bond schemes and conformations obtained in the fifth step. By these methods, the search for stable docking models of biopolymer-ligand molecule complexes can be greatly speeded up and this search can be made even in the case where biopolymers and/or ligand molecules have complicated structures.

Furthermore, the present invention provides methods for searching stable docking models of biopolymer-ligand molecule complex, which comprise the steps of: (1) searching possible hydrogen-bond schemes between a biopolymer and a ligand molecule by preparing possible combination sets of hydrogen-bonding heteroatoms in the ligand molecule with dummy atoms located at the positions of heteroatoms that can be hydrogen-bond partners to hydrogen-bonding functional groups in the biopolymer; (2) estimating the possible hydrogen-bond schemes between the biopolymer and ligand molecule and the possible conformations of a hydrogen-bonding part of the ligand molecule at the same time by comparing the distances between the dummy atoms with the distances between the hydrogen-bonding heteroatoms; and (3) optimizing the conformations of the ligand molecule in such a manner that the positions of the dummy atoms will coincide with the positions of the hydrogen-bonding heteroatoms in the ligand molecule while retaining the hydrogen-bond schemes obtained in the second step and thereafter excluding the conformations of the ligand molecule with intramolecular energies higher than given values; (4) obtaining possible docking models of the biopolymer-ligand molecule complex by changing the coordinates of all atoms of the ligand molecule into the coordinate system of the biopolymer according to the correspondences between the hydrogen-bonding heteroatoms in the ligand molecule and the dummy atoms in combination sets for each of the conformations that have not beer excluded in the third step; (5) excluding the docking models of the hydrogen-bonding part of the ligand molecule with intramolecular energies higher than given values or the intermolecular interaction energies higher than given values between the biopolymer and the hydrogen-bonding part of the ligand molecule, and thereafter optimizing the docking models unexcluded; (6) generating the conformations of a non-hydrogen-bonding part of the ligand molecule for each of the docking models obtained in the fifth step, thereby obtaining new docking models; and (7) excluding the docking models of the whole ligand molecule with intramolecular energies higher than given values and the intermolecular interaction energies higher than given values between the biopolymer and the whole ligand molecule, and thereafter optimizing the complex structures unexcluded. By these methods, accurate docking models can be obtained even if a rather large step of torsion angle is used for systematic conformation generation.

In the present invention, the biopolymers include macromolecules found in organisms, as well as biomimetic molecules thereof.

The hydrogen-bonding functional groups include functional groups or atoms that can be considered to take part in hydrogen-bonds.

The hydrogen-bonding heteroatoms include heteroatoms that constitute hydrogen-bonding functional groups in ligand molecules.

The hydrogen-bonding parts mean those structural parts containing hydrogen-bonding heteroatoms which are in correspondence with dummy atoms and the non hydrogen-bonding parts mean structural parts other than the hydrogen-bonding parts.

BRIEF DESCRIPTION OF DRAWINGS

FIG. 1 is a scheme showing the main steps of the methods of the present invention.

FIG. 8 is a schematic drawing of the binding mode of methotrexate in the crystal structure of the dihydrofolate reductase-methotrexate complex to dihydrofolate reductase (8a) and the binding mode of dihydrofolate to dihydrofolate reductase as predicted from the stereospecificity of the dihydrofolate reductase reaction product (8b).

BEST MODE FOR CARRYING OUT THE INVENTION

Figure 2B:
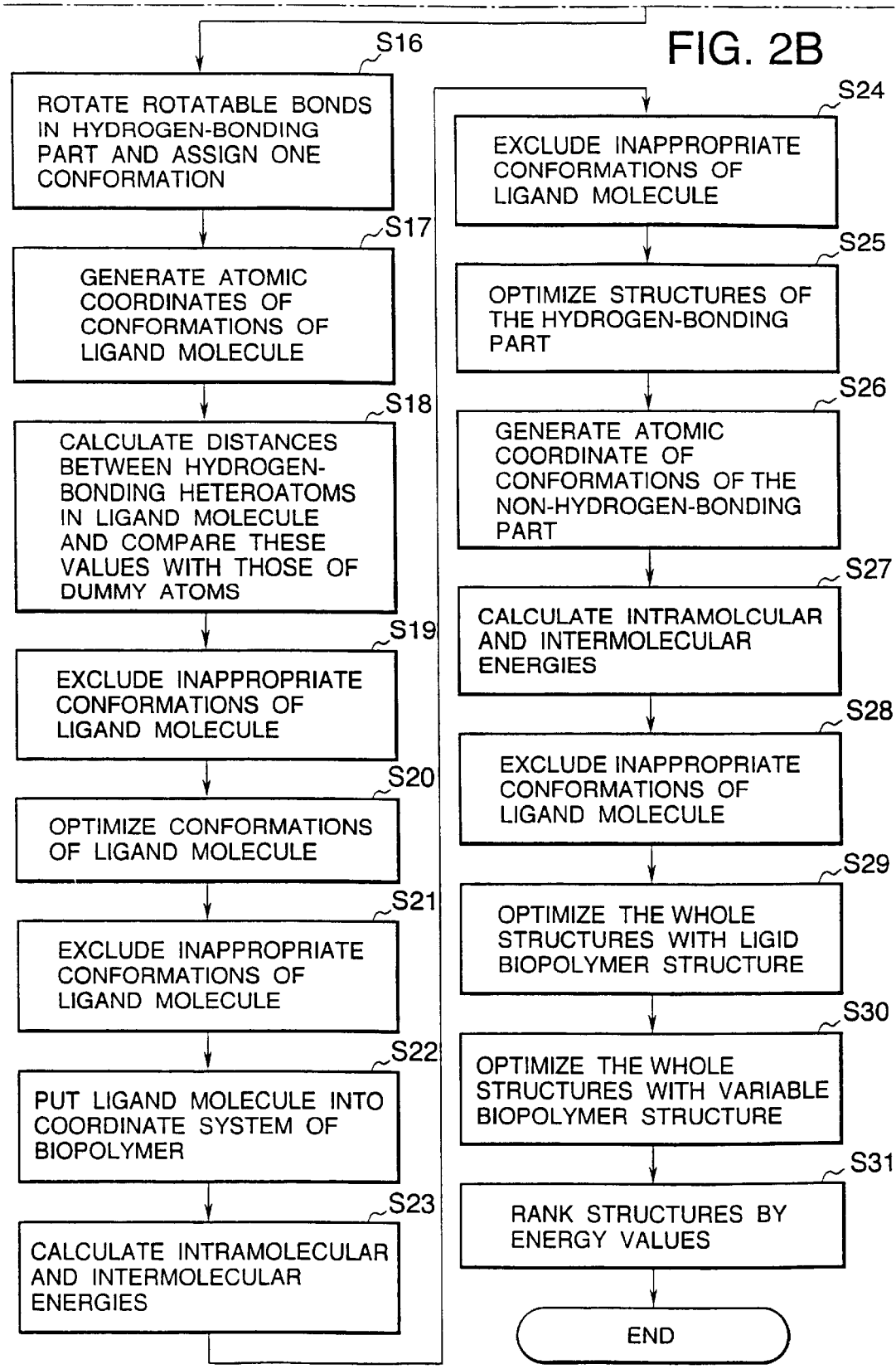
FIG. 2 (including FIGS. 2A and 2B) is a flowchart of the methods of the present invention. In the figure, S represents each step.

A preferred embodiment of the present invention will be explained with reference to the flowchart in FIG. 2. In FIG. 2, S represents each step.

First of all, numbers assigned to biopolymer-constituting atoms and their atomic coordinates other than those of hydrogen atoms are input (S1).

The atomic coordinates of the biopolymer can be obtained by X-ray crystallography or NMR analysis or taken from the Protein Data Bank and the like. Alternatively, the atomic coordinates of a biopolymer model constructed on the basis of the above information can be used. The atomic coordinates are preferably expressed in a three-dimensional coordinate system. In addition, co-factors that are bound to the biopolymer and which play an important role in terms of both structure and function may be treated as a part of the biopolymer and the atomic coordinates of the biopolymer having the co-factors bound thereto may be input to execute the following steps. Examples of the co-factors include coenzymes, water molecule, metal ions and the like.

Then, the atomic coordinates of the amino acid residue-constituting hydrogen atoms in the biopolymer are appended (S2).

In general, the positions of hydrogen atoms in biopolymers cannot be determined by experimental methods such as X-ray crystallographic and NMR analyses. The information on hydrogen atoms is not available from the Protein Data Bank and the like. Therefore, the atomic coordinates of the amino acid residue-constituting hydrogen atoms are calculated on the basis of the structures of the amino acid residues in the biopolymer. The atomic coordinates of the hydrogen atoms whose atomic coordinates cannot be determined uniquely because they are bound to rotatable amino acid residues are preferably calculated on the assumption that they are present in trans-positions Next, atomic charges are appended to the amino acid residue-constituting hydrogen atoms in the biopolymer (S3).

As the values of the atomic charges, documented values which have been determined for various kinds of amino acids such as those published by Weiner can be employed (Weiner, S. J., Kollman, P. A., Case, D. A., Singh, U. C., Ghio, C., Alagona, G., Profeta, S., Jr. and Weiner, P., J. Am. Chem. Soc., 106 (1984) pp. 765–784).

Then, hydrogen-bonding category numbers are assigned to the hydrogen-bonding functional group-constituting heteroatoms present in biopolymer (S4).

The hydrogen-bonding category numbers can be appended according he following Table 1.

TABLE 1

Hydrogen-bonding Category Number and Kinds of Hydrogen-Bonding Functional Group-Constituting Atoms

| Hydrogen-bonding Category Number | Kinds of Hydrogen-Bonding Functional Group-Constituting Atoms |
| --- | --- |
| 1 | $sp^2$ N in Primary Amines |
| 2 | $sp^3$ N in Primary Amines |
| 3 | $sp^3$ N in Ammonium Ions |
| 4 | $sp^2$ N in Amides |
| 5 | $sp^3$ N in Secondary Amines |
| 6 | N in Aromatic Groups |
| 7 | Protonated N in Aromatic Groups |
| 8 | N in Tertiary Amines |
| 9 | Protonated N in Tertiary Amines |
| 10 | O in Hydroxyls Having Rotatable C—O bond |
| 11 | O in Ethers |
| 12 | O in Carbonyls |
| 13 | O in Carboxylate Anions |
| 14 | O in Carboxylic Acids |
| 15 | O in Phosphates |
| 16 | O in Water Molecule |

TABLE 1-continued

Hydrogen-bonding Category Number and Kinds of Hydrogen-Bonding Functional Group-Constituting Atoms

| Hydrogen-bonding Category Number | Kinds of Hydrogen-Bonding Functional Group-Constituting Atoms |
|---|---|
| 17 | S in Mercaptan |
| 18 | S in Thioethers |
| 19 | O in Hydroxyls with fixed hydrogen atom positions |

Then, a ligand-binding region is specified (S5).

As the ligand-binding region, a region containing any site in the biopolymer can be specified. Depending on the purposes, a ligand-binding pocket, a surrounding area of the biopolymer and, if desired, an area containing a site in the biopolymer which is bound to other molecules such as effectors and the like can be specified as a rectangular box as shown in FIG. 1a. The ligand-binding pockets are cavities on the surface of the biopolymer and into which ligand molecules such as substrates, inhibitors and the like are bound.

A part of the functions of the program GREEN can be used in assigning the range of the ligand-binding region (Journal of Computer-Aided Molucular Design, vol. 1, pp.197–210 (1987), Nobuo Tomioka, Akiko Itai, and Yoichi Iitaka).

Three-dimensional grids are generated in the ligand-binding region specified in step S5 and on each three-dimensional grid, grid data is calculated (S6).

The three-dimensional grids are the points generated on three-dimensional lattices at certain intervals within the ligand-binding region in the biopolymer. The grid data includes local physicochemical information on the ligand-binding region such as hydrogen-binding properties, and van der Waals and electrostatic interaction energies that act between the biopolymer and probe atoms and which are calculated on the assumption that a probe atom is present on each three-dimensional grid.

The use of the grid data on the three-dimensional grids makes it possible not only to speed up the approximate calculations of the intermolecular interactions between the biopolymer and ligand molecule to be performed in the following steps but also to determine reasonably the positions of dummy atoms to be set in the following steps. As a result, one can search all possible biopolymer-ligand molecule docking models in a short time.

The three-dimensional grids may be generated at intervals of 0.3–2.0 angstroms, preferably 0.3–0.5 angstroms in the region specified in step S5.

As the probe atoms, all kinds of atoms contained in compounds that are potential ligand molecules are preferably employed.

The van der Waals interaction energy that acts between the biopolymer and each probe atom located on i-th three-dimensional grid can be calculated by a conventional atom-pair type calculation using an empirical potential function. As the empirical potential function, the Lennard-Jones type function represented by the following equation can be used.

$$G_{vdw,i} = \sum_{j}^{NN} (A/r_{ij}^{12} - B/r_{ij}^{6})$$

where NN is the total number of biopolymer atoms, j is the sequential number for the biopolymer atoms. A and B are parameters for determining the potential energy dependent on the atomic distance $r_{ij}$; and $r_{ij}$ is the atomic distance between the i-th grid point and the j-th atom in the biopolymer.

The van der Waals interaction energy between a ligand molecule and biplolymer, when the ligand molecule is placed in the grid region, can be calculated by the following equation:

$$E_{vdw} = \sum_{k}^{N} G_{vdw}(k)$$

where k is the sequential number for the ligand atom, N is the total number of atoms in the ligand molecule, and $G_{vdw}(k)$ is the van der Waals interaction energy of atom k.

As the parameters A and B, the values published by Weiner can be used (Weiner, S. J. Kollman, P. A., Case, D. A., Singh, U. C., Ghio, C., Alagona, G., Profeta, S., Jr. and Weiner, P., J. Am. Chem. Soc., 106 (1984) pp. 765–784).

The electrostatic interaction energy between each probe atom located on i-th three-dimensional grid and the biopolymer can be calculated by the following equation:

$$G_{elc,i} = \sum_{j} Kq_{i}/\varepsilon r_{ij}$$

where i, j and $r_{ij}$ are as defined above, $q_j$ is the atomic charge on the j-th atom in the biopolymer, K is a constant for converting an energy unit and $\varepsilon$ is a dielectric constant.

The dielectric constant may be a fixed value but it preferably is a value depending on $r_{ij}$ as proposed by Warshel (Warshel, A., J. Phys. Chem., 83 (1979) pp.1640–1652).

The electrostatic interaction energy between the ligand molecule and biopolymer, when the ligand molecule is placed in the grided region, can be calculated by the following equation:

$$E_{elc} = \sum_{k}^{N} q_{k} G_{elc}(k)$$

where k and N are as defined above, $G_{elc}(k)$ is the electrostatic interaction energy of atom k and $q_k$ is the atomic charge on atom k.

The hydrogen-bonding flag shows that a hydrogen-bond can be formed with the hydrogen-bonding functional group in the biopolymer if a hydrogen-donor or hydrogen-acceptor atom is located on the three-dimensional grid.

The hydrogen-bonding flag for each three-dimensional grid can be obtained as follows:

If distance DP between three-dimensional grid P and hydrogen(H)-donor atom D present in the biopolymer is the distance that allows for the formation of a hydrogen-bond (e.g., 2.5–3.1 angstroms) and if angle of the vector DH and PH which is made by P, hydrogen H and D is the angle that allows for the formation of a hydrogen-bond (e.g., at least 30°), it can be judged that this three-dimensional grid has hydrogen-donor flag. Similarly, if distance PA between three-dimensional grid P and hydrogen-acceptor atom A present in the biopolymer is the distance that allows for the formation of a hydrogen-bond and if angle of A-L and L-P which is made by P, a lone electron pair L and A is the angle that allows for the formation of a hydrogen-bond, it can be judged that this three-dimensional grid has hydrogen-acceptor flag. If a three-dimensional grid has neither hydrogen-donor flag nor hydrogen-acceptor flag, it can be judged that this three-dimensional grid has no hydrogen-bonding flag. The hydrogen-bonding flag can be expressed by number 1 on three-dimensional grid having hydrogen-acceptor flag, number 2 on three-dimensional grid having hydrogen-donor flag, and number 0 on three-dimensional grid having no hydrogen-bonding flag.

Among hydrogen-bonding functional groups in the biopolymer in the region specified in step S5, several ones which are expected to form hydrogen-bonds with the ligand molecule are selected (S7).

In the case where many hydrogen-bonding functional groups are present, they are selected depending on the degree of importance.

A dummy atom or dummy atoms to each of the hydrogen-bonding functional groups selected in step S7 are generated on the basis of the hydrogen-bonding flags on the three-dimensional grids which is calculated in step S6 (S8).

In this step, a region in which a hydrogen-bond can be formed with each of the hydrogen-bonding functional groups selected in step S7 (hereinafter referred to as "hydrogen-bonding region") may first be determined on the basis of the hydrogen-bonding flags of the three-dimensional grids calculated in step S6 and then a dummy atom is located outside the van der Waals radii of other atoms at the center of the three-dimensional grids with the same hydrogen-bonding flag consisting of e.g., 5–20 three-dimensional grids. The hydrogen-bonding region is a region that is constituted with a group of neighboring three-dimensional grids that have the same hydrogen-bonding flag arisen from the same functional group.

To the dummy atom, the same hydrogen-bonding flag is appended as those of the three-dimensional grids at the center of which the dummy atom is located.

Two or more dummy atoms or no dummy atom may be set for one hydrogen-bonding functional group.

Then, the sequential number, atom name, atom type number, atomic coordinates and atomic charge are input on each atom that constitutes the ligand molecule and if the atom is a hydrogen-bonding heteroatom, its hydrogen-bonding category number is also input (S9).

The atom type of the ligand atom is preferably taken from the Weiner's assignment (Weiner, S. J., Kollman, P. A., Case, D. A., Singh, U. C., Ghio, C., Alagona, G., Profeta, S., Jr. and Weiner, P., J. Am. Chem. Soc., 106 (1984) pp.765–784), if the AMBER potential parameters are used for grid data calculation and energy calculation using grid data.

The atomic coordinates of the ligand molecule can be obtained by the structural analysis of its unbound crystal or taken from Cambridge Crystallographic database or modelled by model building procedures based on the crystal structure or energy calculations. As regards the conformation that is constructed from the ligand molecule, there is no requirement for the conformation, only if accurate geometric data such as bond lengths, bond angles and the like are provided. However, in order to assure that the atomic charge on each ligand atom is calculated as accurately as possible, it is preferred to use atomic coordinates reasonably stable also in unbound states.

The atomic charge on each ligand atom can be calculated by molecular orbital calculations using the MNDO method or the AMI method in the MOPAC program.

The hydrogen-bonding category numbers of the hydrogen-bonding heteroatoms in the ligand molecule can be given according to the above-described Table 1.

Stable binding modes of a ligand molecule to the same biopolymer can be searched by repeating steps S9–S31.

The maximum number ($l_{max}$) and minimum number ($l_{min}$) of hydrogen-bonds that should be considered between the biopolymer and the ligand molecule are selected (S10).

Any numbers may be selected and it is preferred to select values near the number of hydrogen-bonds that is expected from the number of hydrogen-bonds formed between the biopolymer and known ligand molecules.

The bonds whose torsion angles should be rotated in the ligand molecule are selected and their rotation modes are specified (S11).

In the case where the bonds to be rotated are single bonds, it is preferred to specify the rotation mode in which the torsion angles of the bonds are changed systematically with a step of 10°–120°. In the case where the bonds to be rotated are in ring structures, it is preferred to read atomic coordinates of various possible ring structures from a file.

Combination sets of the dummy atoms and the hydrogen-bonding heteroatoms in the ligand molecule are prepared (S12).

If the number of dummy atoms is written as m, the number of heteroatoms in the ligand molecule as n and the number of hydrogen-bonds to be formed between dummy atoms and heteroatoms as i, the number of the combination sets N(i) is:

$$N(i) = {}_mP_i \times {}_nC_i$$

where P represents permutations and C represents combinations. N(i) is all the number of hydrogen-bond schemes to be considered when i hydrogen-bonds are formed.

For all i's that satisfy the relationship $l_{min} \leq i \leq l_{max}$, the process of steps S12–S31 is repeated. As a result, $$\sum_{i=l_{min}}^{l_{max}} N(i)$$

combinations of dummy atoms and hydrogen-bonding heteroatoms in the ligand molecule are all selected. Thus, all possible combinations of the hydrogen-bonds formed by the biopolymer and ligand molecule are selected and thereby the mode of binding of the ligand molecule to the biopolymer can be searched systematically and efficiently.

One of the combination sets of the dummy atom and hydrogen-bonding heteroatom that have been prepared in step S1 is selected (S13).

Combinations in which the hydrogen-binding character (hydrogen-bonding flag) of the dummy atom is not consistent with that of the hydrogen-bonding heteroatom are not selected.

For all combination sets prepared in step S12, steps S13–S30 are iterated.

Then, the distances between the dummy atoms in correspondence with ligand heteroatoms in the combination set selected in step S13 are calculated (S14).

If the number of dummy atoms and that of hydrogen-bonding heteroatoms in the ligand molecule are both 1, the process jumps to step S22 skipping steps S14–S21 and then jumps to step S26 skipping steps S23–S25. If either the number of dummy atoms or that of hydrogen-bonding heteroatoms present in the ligand molecule is 1, the process jumps to step S22 skipping steps S14–S21 .

The ligand molecule is divided into a hydrogen-bonding part and a non-hydrogen-bonding part (S15).

For example, the ligand molecule is divided into the hydrogen-bonding part and the non-hydrogen-bonding part as shown in FIG. 1b.

Rotatable bonds in the hydrogen-bonding part of the ligand molecule divided in step S15 and their rotation modes are assigned (S16).

The atomic coordinates of the conformations of the ligand molecule are generated successively by rotating the bonds selected in step S16 in the rotation modes specified in step S11 (S17).

For each of the generated conformations, subsequent steps S18–S30 are performed.

For the conformation generated in step S17, the distances between the hydrogen-bonding heteroatoms in the ligand molecule that are in correspondence with the dummy atoms in the combination set selected in step S13 are calculated and the obtained values are compared with those of the dummy atoms (S18).

The conformations of the ligand molecule in which the value of F that is the sum of the squares of the difference between the distance between dummy atoms as calculated in step S14 and the distance between the corresponding hydrogen-bonding heteroatoms in the ligand molecule as calculated in step S18 is outside a given range are excluded (S19).

In this step, the possible hydrogen-bond schemes between the biopolymer and ligand molecule and the possible conformations of the ligand molecule can be searched at a time efficiently.

F can be calculated by the following formula:

$$F = \frac{n(n-1)}{2 \sum_i (r_{li} - r_{di})^2},$$

where n is the number of hydrogen-bonds, $r_{di}$ is the i-th distance between dummy atoms, and $r_{li}$ is the i-th distance between hydrogen-bonding heteroatoms in the ligand molecule that are in correspondence with the dummy atoms.

The conformations of the ligand molecule other than those in which F is in the following range are excluded.

$$k_a \cdot \leq F \leq k_a'$$

where $k_a$ is the lower limit of F and $k_a'$ is the upper limit of F.

The value of $k_a$ is preferably 0.6–0.8 and that of $k_a'$ is preferably 1.2–1.4.

For each conformation of each combination set that has not been excluded in step S19, the conformation of the hydrogen-bonding part of the ligand molecule is optimized in such a manner that the value of F is minimized (S20).

In this step, the conformation of the ligand molecule is corrected in such a way that heteroatoms in the ligand achieve a better superposition onto the corresponding dummy atoms.

The conformation of the hydrogen-bonding part of the ligand molecule is optimized by minimizing the value of function F by the Fletcher-Powell method, with the torsion angles of the rotatable bonds in the hydrogen-bonding part of the ligand molecule being treated as variables(R. Fletcher, M. J. D. Powell, Computer J., 6, 163 (1968)).

The intramolecular energy of the hydrogen-bonding part of the ligand molecule that has been optimized in step S20 is then calculated and the conformations having intramolecular energies greater than given values are excluded (S21).

Take, for example, the case of calculating the intramolecular energy of the hydrogen-bonding part of the ligand molecule using a molecular field of AMBER 4.0, the conformations having an intramolecular energy greater than 100 kcal/mol may be excluded.

The ligand molecule is put into the coordinate system of the biopolymer in such a manner that the coordinates of the hydrogen-bonding heteroatoms in the ligand molecule in the conformation obtained in step S21 will coincide with those of the corresponding dummy atoms (S22).

Kabsh's method of least squares can be used in this step (W. Kabsh, Acta. Cryst., A32, 922 (1976) and W. Kabsh, Acta Cryst., A34, 827 (1978)). Thus, the possible hydrogen-bond schemes and the conformations of the hydrogen-bonding part of the ligand molecule can be estimated roughly at the same time.

In the next step, the intermolecular interaction between the biopolymer and the hydrogen-bonding part of the ligand molecule (the sum of a van der Waals interaction energy and an electrostatic interaction energy) and the intramolecular energy of the hydrogen-bonding part of the ligand molecule are calculated (S23).

The intermolecular interaction energy between the biopolymer and the hydrogen-bonding part of the ligand molecule ($E_{inter}$) can be calculated by the following formula:

$$E_{inter} = \sum_k \{G_{vdw}(k) + G_{elc}(k) \cdot q_k\}$$

where $G_{vdw}$ (k) is the van der Waals interaction energy of atom k, $G_{elc}$ (k) is the electrostatic interaction energy of atom k and $q_k$ is the atomic charge on atom k.

The values of $G_{vdw}$ (k) and $G_{elc}$ (k) can be obtained from the grid data of the three-dimensional grid that is the closest to atom k in the ligand molecule.

The intramolecular energy of the hydrogen-bonding part of the ligand molecule ($E_{intra}$) can be calculated by any known method using any known and published force field. For example, $E_{intra}$ can be calculated by the following formula using any known and published force field such as AMBER4.0:

$$E_{intra} = \sum_{Dihedrals} \sum_n V_n/2\{1+\cos(n\Phi-\gamma)\} + \sum_{i<j}(A_{ij}/R_{ij}^{12} - B_{ij}/R_{ij}^6) + \sum_{i<j}(q_i q_j/\varepsilon R_{ij})$$

where $V_n$ is a constant provided for an array of the atomic types of four atoms that constitute the torsion angle, n is a constant representing the symmetry of a potential with respect to torsional rotation, $\phi$ is the torsion angle, $\gamma$ is the phase of a potential with respect to torsional rotation that is provided for an array of the atomic types of four atoms that constitute the torsion angle, $A_{ij}$ and $B_{ij}$ are constants set for a pair of the atomic types of the i-th and j-th atoms in the ligand molecule, $R_{ij}$ is the distance between the i-th and j-th atoms, $q_i$ is the atomic charge on the i-th atom in the ligand molecule, $q_j$ is the atomic charge on the j-th atom in the ligand molecule, and $\epsilon$ is a dielectric constant.

The conformations of the ligand molecule in which the sum of the intermolecular interaction energy and intramolecular energy as calculated in step S23 is greater than a given value are excluded (S24).

For example, it is preferred to exclude the conformations in which the sum of these energies is greater than 1500 kcal/mol.

The structures of the hydrogen-bonding part of the ligand molecule having the conformation that has not been excluded in step S24 are optimized (S25).

The structures of the hydrogen-bonding part of the ligand molecule can be optimized by optimizing the torsion angles of the hydrogen-bonding part of the ligand molecule, the location and orientation of the ligand molecule by structure optimization calculations. For example, the structures of the hydrogen-bonding part of the ligand molecule can be optimized by the Simplex method (HITACHI. Library Program, SOFSM) in such a manner that the total energy ($E_{total}$) as calculated by the following formula is minimized:

$$E_{total} = E_{inter} + E_{intra} + Whb \cdot Nhb \cdot Chb$$

where $E_{inter}$ and $E_{intra}$ are as defined above, $Whb$ is a weight, $Nhb$ is the number of hydrogen-bonds, and $Chb$ is a constant energy value assigned for one hydrogen-bona (e.g., 2.5 kcal/mol).

The conformations of the ligand molecules are generated by rotating the rotatable bonds in the non-hydrogen-bonding part of the ligand molecule in the rotation modes that have been specified in step S11 (S26).

For each of the generated conformations, steps S27–S30 are iterated.

The energy of the intermolecular interaction between the biopolymer and ligand molecule and the intramolecular energy of the ligand molecule are calculated (S27).

The intermolecular interaction and intramolecular energies can be calculated by the same method as in step S23, provided, however, the energies are calculated only for the hydrogen-bonding part of the ligand molecule in step S23 whereas calculations are performed for the whole ligand molecule in step S27.

The conformations of the ligand molecule in which the sum of the intermolecular interaction and intramolecular energies as calculated in step S27 is greater than a given value are excluded (S28).

The upper limit for this energy sum is preferably 1500 kcal/mol.

The structures of the whole ligand molecule having conformations that have not been excluded in step S28 are optimized (S29).

In this step, the stable structures of the biopolymer-ligand molecule complex and the active conformations of the ligand molecule can be obtained.

The structures of the whole ligand molecule can be optimized by the same method as in step S25, provided, however, only the structure of the hydrogen-bonding part of the ligand molecule is optimized in step S25 whereas the structure of the whole ligand molecule is optimized in step S29. The structures of the complex obtained in the steps up to S29 are referred to as "initial docking models".

The structures of the biopolymer-ligand molecule complex are optimized by changing the conformation of the biopolymer (S30).

In the steps up to S29, the biopolymer has been treated as a rigid substance. In step S30, the energies of the initial docking models are minimized by changing the conformation of the biopolymer. The structures of the initial docking models can be optimized by minimizing the energies of the initial docking models using the known energy-minimizing calculation program AMBER. In this step, it is preferred to optimize the whole structures, locating therein all water molecules and other molecules that are supposed to be included in the energy system. The structures obtained in step S20 are referred to as "final docking models".

The energies of the structures of the biopolymer-ligand complex obtained in the steps up to S30 are calculated and the docking models are ranked in the increasing order of energy (S31).

In many cases, the lowest energy docking models of all the final docking models is in good agreement with the structure of the complex that has been elucidated experimentally. Therefore, it will be reasonable to consider the lowest energy docking models as the correct structure of the complex. However, since the order of the energy values of the complexes varies depending on the accuracies of the force field used, the atomic coordinates of the biopolymer and the like, it is preferred to consider not only the lowest energy docking model but also a few more docking models having higher energies.

In a more preferred embodiment of the present invention, if the generation of a large number of dummy atoms is expected from the biopolymer or if the ligand molecule has a very large conformational flexibility or a large number of heteroatoms, information on the ligand molecule is input in step S9 and, thereafter, the partial structure of the ligand molecule is specified and the process steps S10–S24 is performed on the specified partial structure so as to store the combination sets that provide hydrogen-bond schemes impossible in the partial structure, as well as the information on the hydrogen-bonding heteroatoms in the ligand molecule that do not form any hydrogen-bond with dummy atoms. Any partial structure of the ligand molecule can be specified without structural restrictions. Partial structures containing at least three hydrogen-bonding functional groups are preferred and the conformational flexibility thereof can be handled. Then, the process of steps S10–S31 is performed on the whole structure of the ligand molecule, but the combination sets containing the stored hydrogen-bonding heteroatoms and those of the stored combination sets of dummy atoms and hydrogen-bonding heteroatoms are excluded from the combination sets prepared in step S12. As a result, the number of the combination sets and conformations to be checked decreases and thereby the time to search the structures of stable biopolymer-ligand molecule complex is greatly shortened. This method is referred to as the "Pre-Pruning method"(hereinafter described as the "PP method").

The PP method is based on the presumption that any hydrogen-bond schemes and ligand conformations that are impossible in the partial structure of the ligand molecule are also impossible in the structure of the whole ligand molecule. According to the PP method, the searching time is further shortened without affecting the precision and reliability of the docking models of biopolymer-ligand molecule thus obtained.

EXAMPLE

In order to show their effectiveness, the methods of the present invention were applied to the search for the structures of dihydrofolate reductase-inhibitor/substrate complexes. Dihydrofolate reductase is one of the enzymes that are being studied as targets of clinical drugs all over the world and the crystal structures of their complexes with various inhibitor molecules have been analyzed. For example, dihydrofolate reductase-inhibitor methotrexate complex is often used as a model in methodological studies for the analysis of stable complex structures in the world because its crystal structure was analyzed experimentally.

As the atomic coordinates of dihydrofolate reductase (hereinafter referred to as "DHFR"), the values taken from the atomic coordinates of the binary complex of *E. coli* DHFR and methotrexate available from the Protein Data Bank Entry 4DFR were used. The atomic coordinates of a co-factor $NADP^+$ molecule were appended to the atomic coordinates of the binary complex on the basis of the crystal structure of the ternary complex of DHFR, folic acid and NADP$^+$. All water molecules other than the two water molecules that are too strongly bound to DHFR to be removed by chemical methods were eliminated from the atomic coordinates of the binary complex. One of the two uneliminated water molecules is bound to tryptophan 21 and aspartic acid 26 through hydrogen-bonds and the other is bound to leucine 114 and threonine 116 through hydrogen-bonds (see FIG. 8).

The atomic coordinates of the amino acid-constituting hydrogen atoms present in DHFR were calculated by PDB-FIL which is one of the programs that constitute GREEN. Atomic charges were imparted to the amino acid-constituting atoms present in DHFR on the basis of the results of Weiner's ab initio calculation (Weiner, S. J., Kollman, P. A., Case, D. A., Singh, U. C., Ghio, C., Alagona, G., Profeta, S., Jr. and Weiner, P., J. Am. Chem. Soc., 106 (1984) pp.765–784). The carboxyl side chain of aspartic acid 27 was assumed to be ionized to a caboxylate anion. Hydrogen-bonding category numbers were assigned by PDBFIL to the heteroatoms of the hydrogen-bonding functional groups in DHFR.

In the crystal structure of the binary complex of dihydrofolate reductase and methotrexate, a rectangular prismatic region having a size of 12.8×16.8 ×11.6 Å$^3$ around a pocket in which the inhibitor methotrexate was bound was specified as the ligand-binding region.

Three-dimensional grids were generated in the rectangular prismatic region at intervals of 0.4 Å and grid data was calculated for each of the three-dimensional grids. As probe atoms, hydrogen, carbon, nitrogen and oxygen atoms were employed which were included in methotrexate.

Ten hydrogen-bonding functional groups in both the side and main chains of the amino acids of DHFR that stretch out into the rectangular prismatic region were selected. Eleven dummy atoms were set for the ten hydrogen-bonding functional groups.

As ligand molecules, inhibitor methotrexate (hereinafter referred to as "MTX") and substrate dihydrofolate (hereinafter referred to as "DHF") were selected.

Example 1

Methotrexate Molecule

The terminal carboxyl group of MTX molecule was removed to simplify the example and the following procedure was performed.

Figure 3A:
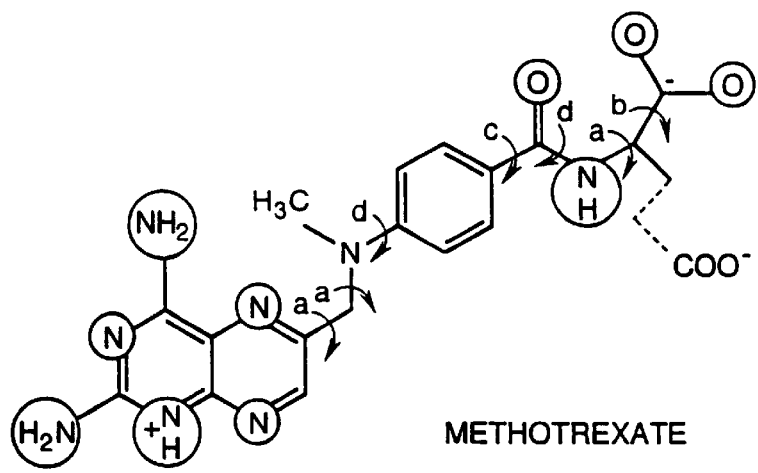
FIG. 3 shows the molecular structures of methotrexate (MTX) and dihydrofolate (DHF). In the figure, the circled atoms are hydrogen-bonding heteroatoms and bonds with arrows a–d are bonds to be rotated systematically.
Figure 3B:
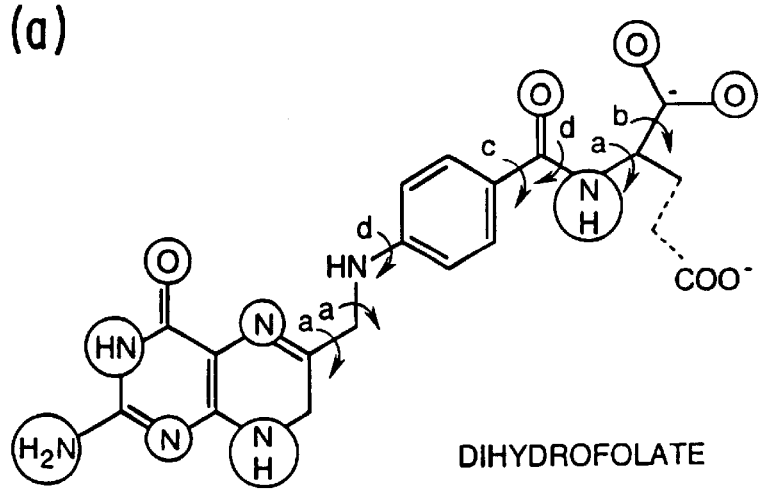

As the atomic coordinates of MTX, the atomic coordinates of the unbound crystal structure available from Cambridge Crystallographic Database were input. The atomic charge on each atom of MTX was calculated by the MNDO method in the MOPAC program. Since the nitrogen at position 1 in the pteridine ring of MTX was susceptible to protonation, the atomic charge thereon was calculated on the assumption that it was protonated. In the structures shown in FIG. 3, the encircled heteroatoms were selected as the hydrogen-bonding heteroatoms and the hydrogen-bonding category numbers were assigned thereto. In the MTX molecular structure shown in FIG. 3, bond a was rotated at intervals of 60° in the range of 0°–360°, bond b was rotated at intervals of 60° in the range of 0°–180°, bond c was assigned as either 0° or 180°, and bond d was set to 180° so as to generate the conformations of MTX molecule (the arrows in FIG. 3 show the rotated bonds).

This method provides enormous numbers of the combinations N(i) of hydrogen-bonds in forming i (i.e., i=4–7) hydrogen-bonds as follows:

$N(7) = {}_{11}P_7 \times {}_{10}C_7 = 199{,}584{,}000$ $N(6) = {}_{11}P_6 \times {}_{10}C_6 = 69{,}854{,}400$ $N(5) = {}_{11}P_5 \times {}_{10}C_4 = 13{,}970{,}880$ $N(4) = {}_{11}P_4 \times {}_{10}C_4 = 207{,}900$ All structures of the MTX molecule could be docked to DHFR at a stretch (the time required for processing from the entry of the atomic coordinates of MTX molecule to the optimization of the complex structures was about 30 hours). However, the time required was shortened (the time required for processing from the entry of the atomic coordinates of MTX molecule to the optimization of the complex structures was about 30 minites) by using the PP method in which the partial structure from the pteridine ring to the benzene ring in MTX molecule was docked to DHFR (requiring about 4 minutes) and, on the basis of the results, stable docking models were searched considering the whole MTX molecule structure. The same stable docking models were obtained in both cases.

Figure 4:
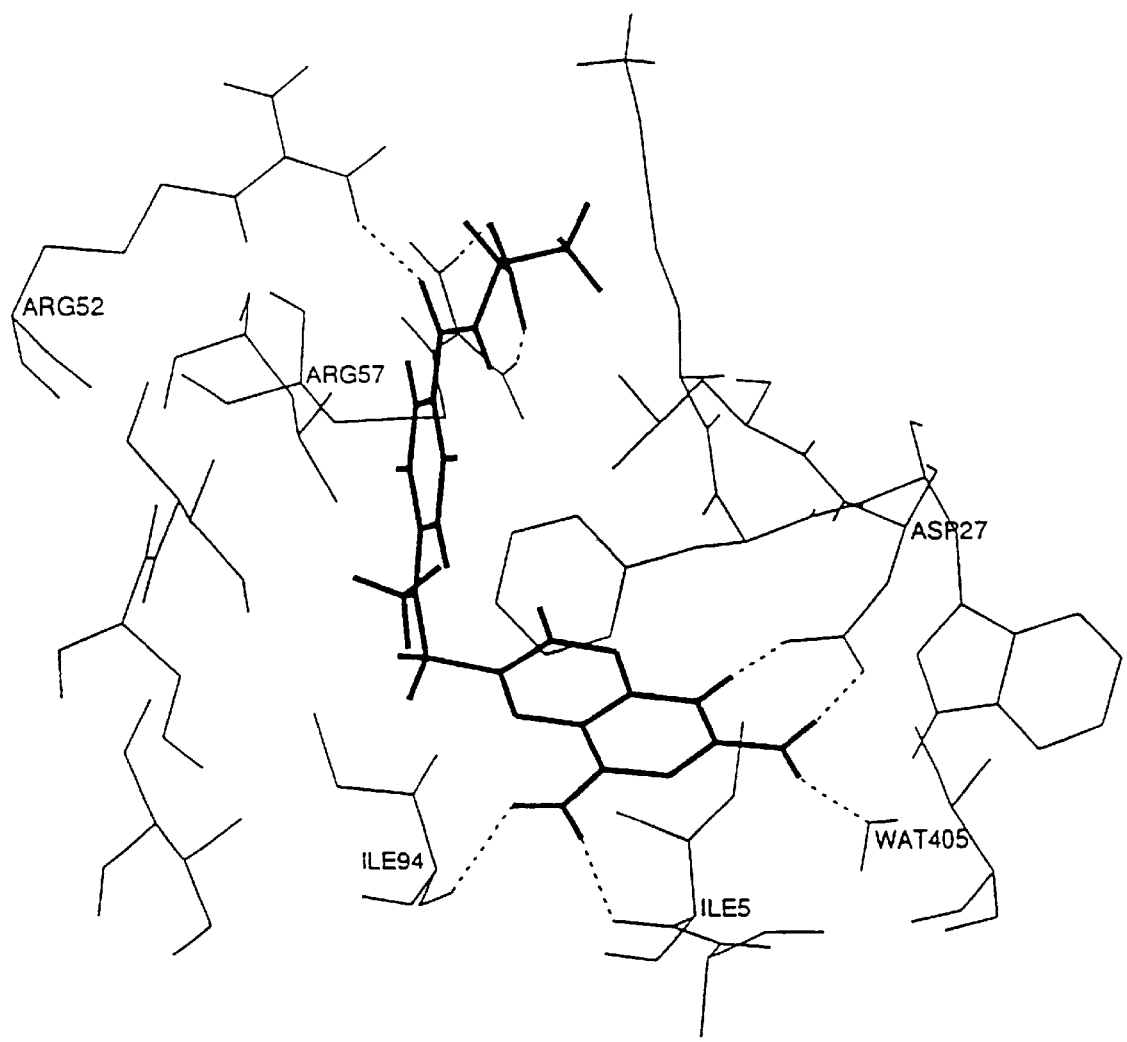
FIG. 4 shows the lowest energy docking model of a dihydrofolate reductase-methotrexate complex. In the figure, the structure drawn in bold lines is the molecular structure of methotraxate and the structure drawn in fine lines is a part of the molecular structure of dihydrofolate reductase.
Figure 5:
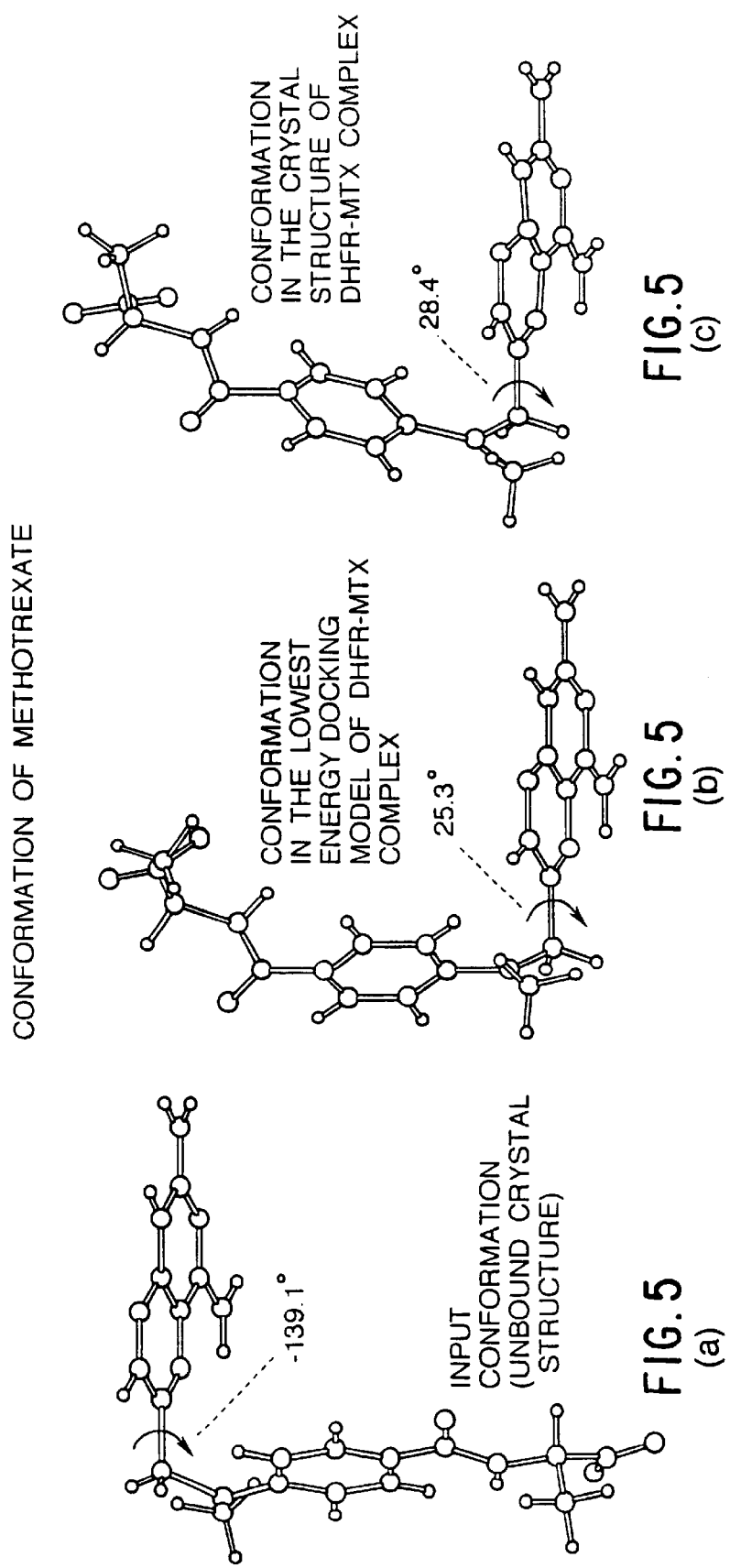
FIG. 5 shows the input conformation of methotrexate which is found in the crystal structure of the unbound form (5a), the conformation of methotrexate in the lowest energy docking model of the dihydrofolate reductase-methotrexate complex (5b), and the conformation of methotrexate in the crystal structure of the dihydrofolate reductase-methotrexate complex (5c).

Out of the 11 initial docking models obtained, five models were selected in the increasing order of energy and the energy of each model was minimized by the AMBER program to obtain final docking models. The energy value and the number of hydrogen-bonds of each model were changed and the ranks of some models were changed by the minimization of the energy using the AMBER program. These facts suggest that the effect of the local adaptation of the biopolymer is significant. Table 2 shows the number of hydrogen-bonds and the total energy of stable complexes in higher ranks that were finally obtained. FIG. 4 shows the lowest energy docking model (−176.71 kcal/mol). In FIG. 4, the bold lines represent the MTX molecule structure and the dotted lines a part of the DHFR molecule structure. The binding mode of the DHFR-MTX complex in this docking model reproduces precisely the binding mode of the complex in the crystal structure obtained by X-ray crystallographic analysis. FIG. 5 shows the conformation of the MTX molecule in the lowest energy docking model (FIG. 5b) together with the input conformation which is the unbound crystal structure (FIG. 5a) and that found in the DHFR-MTX complex in the crystal structure (FIG. 5c). As is clear from FIG. 5, the torsion angle of C5-C6-C9-C10 of the input conformation is 139.1° whereas it is 25.3° in the lowest energy docking model and 28.4° in the crystal structure of the DHFR-MTX complex. The conformation of the MTX molecule in the lowest energy docking model changed greatly from the input structure, showing a very high degree of agreement with the conformation in the crystal structure of the complex.

Example 2

Dihydrofolic Acid Molecule

Figure 6:
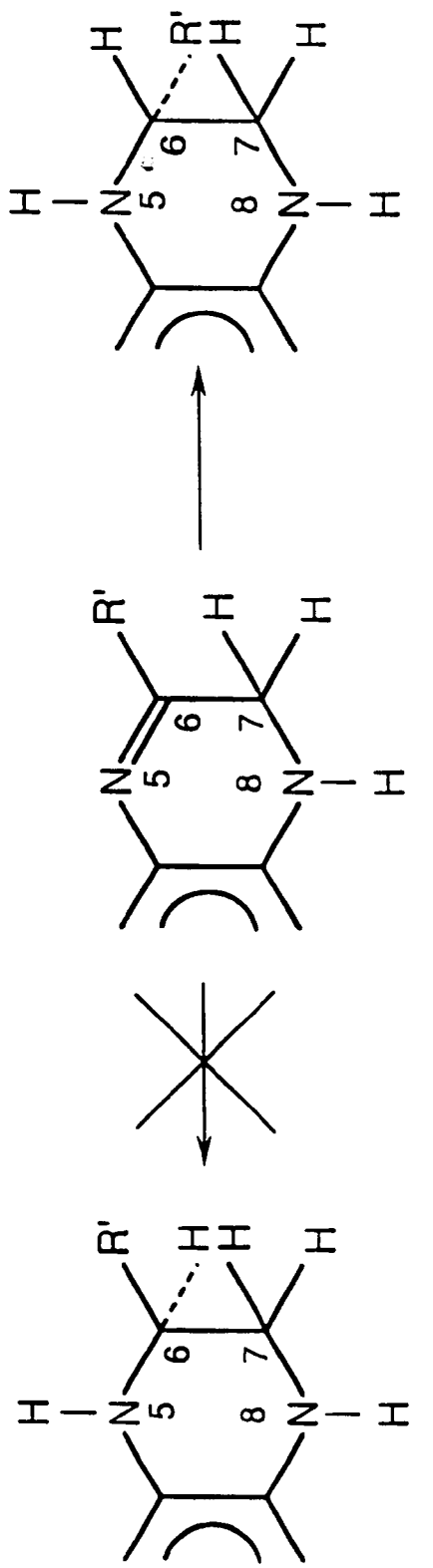
FIG. 6 shows a stereospecific reaction of dihydrofolate reductase.

Although the binding mode of DHFR to its substrate DHF has not yet been identified by X-ray analysis, it has been predicted from the stereospecifity of tetrahydrofolic acid that is the product of enzymatic reaction for the following reasons that the DHF molecule binds to the enzyme in a different mode from that of binding with MTX: It is known that the hydrogen at position C6 in the tetrahydrofolic acid that is produced by the reducing action of DHFR is derived as a hydride ion from coenzyme NADPH. If it is assumed that the binding mode of the DHFR-DHF complex is the same as that of the MTX and DHFR molecules in the crystal structure of the ternary DHFR-MTX-NADPH complex obtained by X-ray analysis, tetrahydrofolic acid with opposite chirality should be produced. This strongly indicated that pteridine of DHF molecule is reversed from that of MTX (see FIG. 6).

In Example 2, the structures of stable DHFR-DHF complexes were searched without any preconception by the same method as in Example 1, using the atomic coordinates of DHF that were prepared on the basis of the atomic coordinates of the crystal structure of unbound MTX. The atomic charge on each atom of DHF was calculated by the same method as in Example 1. The encircled heteroatoms in FIG. 3 were selected as hydrogen-bonding heteroatoms and hydrogen-bonding category numbers were assigned thereto.

Figure 7:
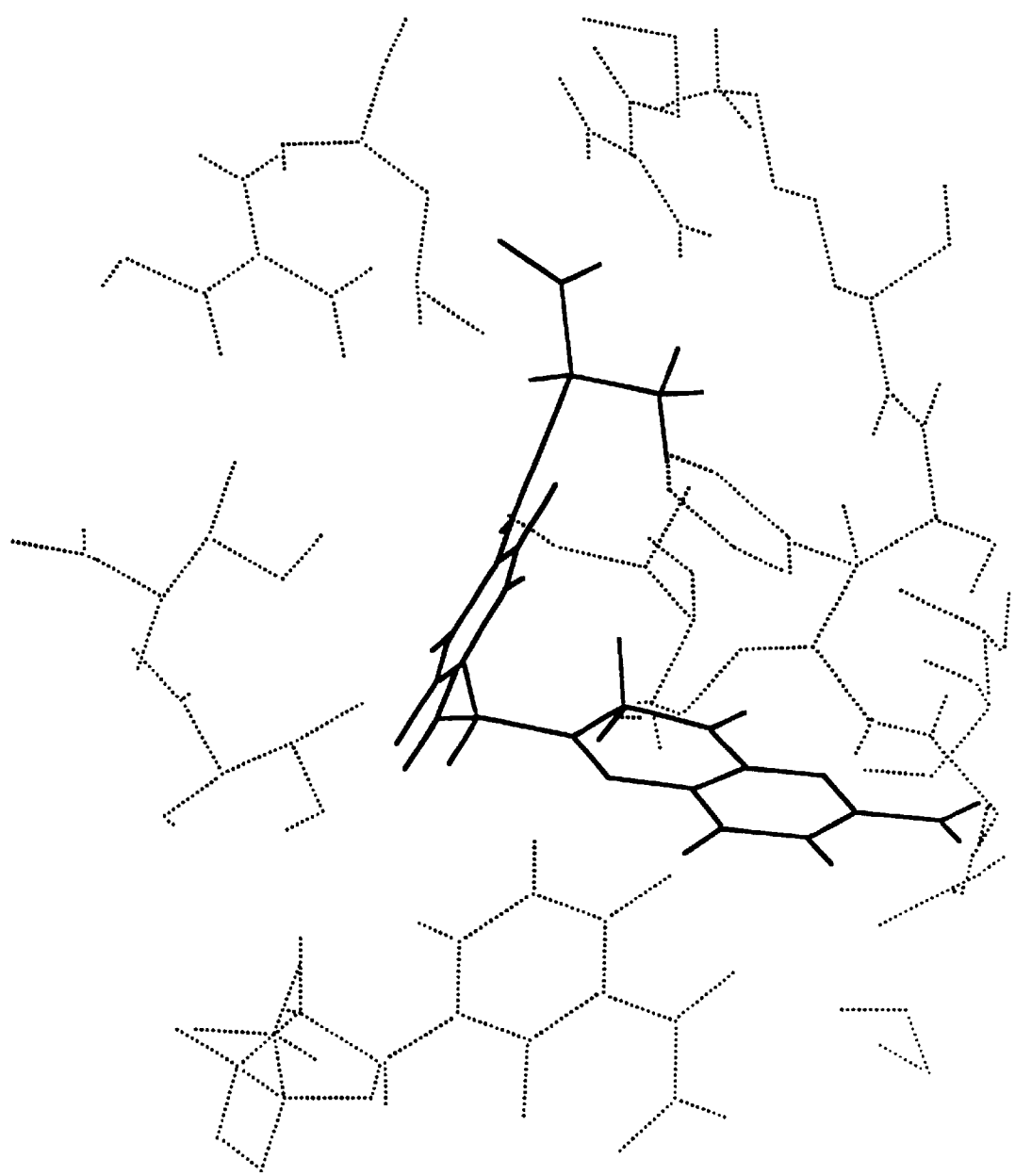
FIG. 7 shows the lowest energy docking model of the dihydrofolate reductase-dihydrofolate complex that is obtained by the method of the present invention. In the figure, the structure drawn in bold lines is the molecular structure of dihydrofolate and the structure drawn in dotted lines is a part of the molecular structure of dihydrofolate reductase.

Table 2 shows the number of hydrogen-bonds and the total energy of the stable docking models in higher ranks that were finally obtained. FIG. 7 shows the lowest energy docking model (−173.46 kcal/mol). In FIG. 7, the bold lines represent the DHF molecule and the dotted lines represent a part of the DHFR molecule. In the conformation of DHF in the lowest energy docking model, the plane of the pteridine ring was reversed from that of MTX in the crystal structure of the DHFR-MTX complex. The mode of binding of DHF to DHFR in the lowest energy docking model agreed well with that estimated from the stereospecifity of the DHFR enzymatic reaction product (FIG. 8b). This mode of DHF binding to DHFR provides a reasonable explanation of the stereospecifity of the DHFR enzymatic reaction (see FIG. 6). The conformation of DHF in the lowest energy docking model was very close to the conformation of substrate analogue folic acid in the crystal structure of folic acid and DHFR complex.

The results thusly show the effectiveness of the methods of the present invention.

TABLE 2

Dihydrofolate Reductase-Ligand Docking Models

| | Initial Docking Model | | Final Docking Model | |
|---|---|---|---|---|
| Ligand | The Number of Hydrogen-bonds | Total Energy (kcal/mol) | The Number of Hydrogen-bonds | Total Energy (kcal/mol) |
| Methotrexate | 4 | −85.01 | 8 | −176.71 |
| | 3 | −67.32 | 6 | −158.15 |
| | 3 | −61.27 | 6 | −141.91 |
| Dihydrofolate | 3 | −80.96 | 6 | −159.20 |
| | 3 | −76.20 | 8 | −173.46 |
| | 3 | −63.38 | 7 | −161.45 |

According to the methods of the present invention, the structures of stable biopolymer-ligand molecule complexes can be searched in a short time.

According to the methods of the present invention, a few biopolymer-ligand docking models including the lowest energy docking model can be efficiently searched from all possible structures of the biopolymer-ligand molecule complex.

In addition, according to the methods of the present invention, the structures of stable biopolymer-ligand molecule complexes can be searched without intervention by the user's subjectivity.

Furthermore, according to the methods of the present invention, the structures of stable biopolymer-ligand molecule complexes can be searched with high degrees of reliability and reproducibility.

Moreover, according to the present invention, the structures of stable biopolymer-ligand molecule complexes can be searched based on a sufficient quantitative estimation of intermolecular interactions, taking into account the degree of freedom in the conformation of a ligand molecule.

In addition, according to the methods of the present invention, the structures of stable biopolymer-ligand molecule complexes can be searched even in the case where the number of hydrogen-bonds between the biopolymer and ligand molecule is small, for example, 1.

Industrial Applicability

In accordance with the methods of the present invention, the mode in which newly designed ligand molecules are prone to bind with target biopolymers and the degree of the stabilities of the complexes can be predicted and thereby drugs and active compounds can be designed rationally and efficiently.

In addition, new lead compounds can be identified from great many compounds in databases as candidates for ligands to a target biopolymer by applying the methods of the present invention.

What is claimed is:

1. A method which comprises:

inputting three-dimensional coordinates for each atom of a biopolymer as well as atomic element, bond-type of covalent bonds and three-dimensional coordinates for each atom of a ligand;

covering all possible docking structures between said biopolymer and said ligand while changing the conformation of said ligand by rotating torsion angles for each binding scheme; and outputting information about three-dimensional coordinates for each atom of the ligand in one or more stable docking structures including the most stable docking structure relative to the biopolymer, the stability of said docking structures, as well as the binding modes and conformations of the ligand in said structures, wherein possible binding modes between the biopolymer and the ligand are covered by examining all combinations of correspondences between dummy atoms and heteroatoms in the ligand instead of changing relative positions and orientations between the two molecules, said dummy atoms being preset at the positions of heteroatoms that can be hydrogen-bonded with the hydrogen bonding groups in the biopolymer.

2. A method which comprises:

inputting three-dimensional coordinates for each atom of a biopolymer as well as atomic element, bond-type of covalent bonds and three-dimensional coordinates for each atom of a ligand;

covering all possible docking structures between said biopolymer and said ligand while changing the conformation of said ligand by rotating torsion angles for each binding scheme; and outputting information about three-dimensional coordinates for each atom of the ligand in one or more stable docking structures including the most stable docking structure relative to the biopolymer, the stability of said docking structures, as well as the binding modes and conformations of the ligand in said structures, wherein possible hydrogen-bonding schemes between the biopolymer and the ligand and conformations of the ligand are roughly estimated while maintaining both molecules in separate coordinate systems without examining their docking structures, by utilizing rough matching of distances among dummy atoms and those among heteroatoms of the ligand, said dummy atoms being preset at the positions of heteroatoms that can be hydrogen-bonded with the hydrogen bonding groups in the biopolymer.

3. A method which comprises:

inputting three-dimensional coordinates for each atom of a biopolymer as well as atomic element, bond-type of covalent bonds and three-dimensional coordinates for each atom of a ligand;

covering all possible docking structures between said biopolymer and said ligand while changing the conformation of said ligand by rotating torsion angles for each binding scheme; and outputting information about three-dimensional coordinates for each atom of the ligand in one or more stable docking structures including the most stable docking structure relative to the biopolymer, the stability of said docking structures, as well as the binding modes and conformations of the ligand in said structures, wherein likely hydrogen-bonding schemes and conformations of the ligand are selected by optimizing torsion angles of possible conformations of the ligand estimated together with hydrogen-bonding schemes so that heteroatoms in the ligand match the corresponding dummy atoms and by rejecting conformations with bad matching score, while maintaining both the biopolymer and the ligand in separate coordinate systems without examining their docking structures, said dummy atoms being preset at the positions of heteroatoms that can be hydrogen-bonded with the hydrogen bonding groups in the biopolymer.

4. A method which comprises:

inputting three-dimensional coordinates for each atom of a biopolymer as well as atomic element, bond-type of covalent bonds and three-dimensional coordinates for each atom of a ligand;

covering all possible docking structures between said biopolymer and said ligand while changing the conformation of said ligand by rotating torsion angles for each binding scheme; and outputting information about three-dimensional coordinates for each atom of the ligand in one or more stable docking structures including the most stable docking structure relative to the biopolymer, the stability of said docking structures, as well as the binding modes and conformations of the ligand in said structures, wherein possible docking structures are constructed by putting the ligand in the likely conformations into the coordinate system of the biopolymer by superposing corresponding pairs of dummy atoms and heteroatoms of the ligand in likely hydrogen-bonding schemes estimated together with the likely conformations of the ligand, said dummy atoms being preset at the positions of heteroatoms that can be hydrogen-bonded with the hydrogen bonding groups in the biopolymer.

5. A method which comprises:

inputting three-dimensional coordinates for each atom of a biopolymer as well as atomic element, bond-type of covalent bonds and three-dimensional coordinates for each atom of a ligand;

selecting stable docking structures between said biopolymer and said ligand based on calculated energies while changing the conformation of said ligand by rotating torsion angles for each hydrogen-bonding scheme; and outputting information about three-dimensional coordinates for each atom of the ligand in one or more stable docking structures including the most stable docking structure relative to the biopolymer, the stability of said docking structures, as well as the binding modes and conformations of the ligand in said structures, wherein possible binding modes between the biopolymer and the ligand are covered by examining all combinations of correspondences between dummy atoms and heteroatoms in the ligand instead of changing relative positions and orientations between the two molecules, said dummy atoms being preset at the positions of heteroatoms that can be hydrogen-bonded with the hydrogen bonding groups in the biopolymer.

6. A method which comprises:

inputting three-dimensional coordinates for each atom of a biopolymer as well as atomic element, bond-type of covalent bonds and three-dimensional coordinates for each atom of a ligand;

selecting stable docking structures between said biopolymer and said ligand based on calculated energies while changing the conformation of said ligand by rotating torsion angles for each hydrogen-bonding scheme; and outputting information about three-dimensional coordinates for each atom of the ligand in one or more stable docking structures including the most stable docking structure relative to the biopolymer, the stability of said docking structures, as well as the binding modes and conformations of the ligand in said structures, wherein possible hydrogen-bonding schemes between the biopolymer and the ligand and conformations of the ligand are roughly estimated while maintaining both molecules in separate coordinate systems without examining their docking structures, by utilizing rough matching of distances among dummy atoms and those among heteroatoms of the ligand, said dummy atoms being preset at the positions of heteroatoms that can be hydrogen-bonded with the hydrogen bonding groups in the biopolymer.

7. A method which comprises:

inputting three-dimensional coordinates for each atom of a biopolymer as well as atomic element, bond-type of covalent bonds and three-dimensional coordinates for each atom of a ligand;

selecting stable docking structures between said biopolymer and said ligand based on calculated energies while changing the conformation of said ligand by rotating torsion angles for each hydrogen-bonding scheme; and outputting information about three-dimensional coordinates for each atom of the ligand in one or more stable docking structures including the most stable docking structure relative to the biopolymer, the stability of said docking structures, as well as the binding modes and conformations of the ligand in said structures, wherein likely hydrogen-bonding schemes and conformations of the ligand are selected by optimizing torsion angles of possible conformations of the ligand estimated together with hydrogen-bonding schemes so that heteroatoms in the ligand match the corresponding dummy atoms and by rejecting conformations with bad matching score, while maintaining both the biopolymer and the ligand in separate coordinate systems without examining their docking structures, said dummy atoms being preset at the positions of heteroatoms that can be hydrogen-bonded with the hydrogen bonding groups in the biopolymer.

8. A method which comprises:

inputting three-dimensional coordinates for each atom of a biopolymer as well as atomic element, bond-type of covalent bonds and three-dimensional coordinates for each atom of a ligand;

selecting stable docking structures between said biopolymer and said ligand based on calculated energies while changing the conformation of said ligand by rotating torsion angles for each hydrogen-bonding scheme; and outputting information about three-dimensional coordinates for each atom of the ligand in one or more stable docking structures including the most stable docking structure relative to the biopolymer, the stability of said docking structures, as well as the binding modes and conformations of the ligand in said structures, wherein possible docking structures are constructed by putting the ligand in the likely conformations into the coordinate system of the biopolymer by superposing corresponding pairs of dummy atoms and heteroatoms of the ligand in likely hydrogen-bonding schemes estimated together with the likely conformations of the ligand, said dummy atoms being preset at the positions of heteroatoms that can be hydrogen-bonded with the hydrogen bonding groups in the biopolymer.

* * * * *

UNITED STATES PATENT AND TRADEMARK OFFICE
CERTIFICATE OF CORRECTION

PATENT NO. : 6,308,145 B1  
DATED : October 23, 2001  
INVENTOR(S) : Itai et al.

It is certified that error appears in the above-identified patent and that said Letters Patent is hereby corrected as shown below:

<u>Title page,</u>  
Item [62], the Related U.S. Application Data should read:

--         Related U.S. Application Data

[62] Division of application No. 08/307,581 filed as No. PCT/JP93/00365, filed on Mar. 26, 1993, now Patent No. 5,642,292. --

Item [30], the Foreign Application Priority information should read:

-- [30]      Foreign Application Priority Data

Mar. 27, 1992    (JP)…………………………...4-119484

Signed and Sealed this

Second Day of July, 2002

*Attest:*

JAMES E. ROGAN  
*Director of the United States Patent and Trademark Office*

*Attesting Officer*